Figure 1:
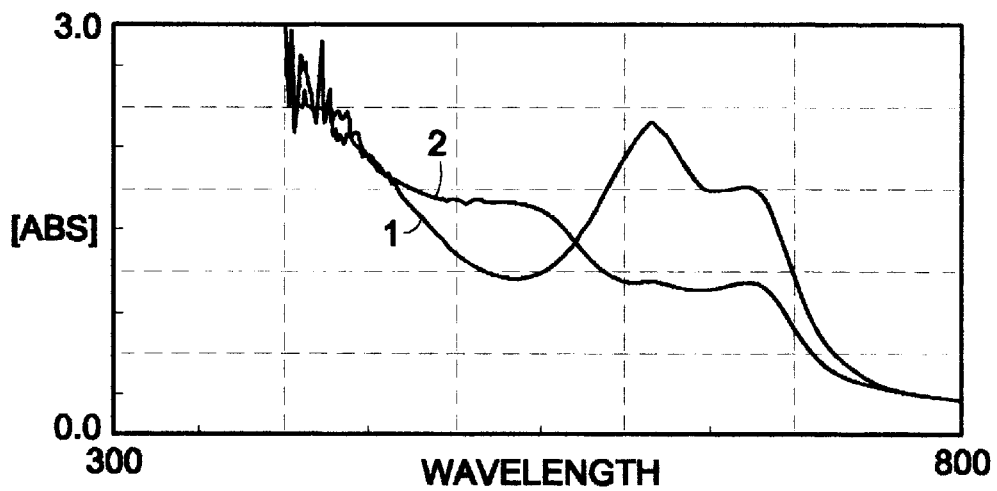

United States Patent
Bell

Patent Number: 6,165,796
Date of Patent: Dec. 26, 2000

[54] PIPETTABLE ION DETECTOR AND METHOD

[75] Inventor: Michael L. Bell, Fullerton, Calif.

[73] Assignee: Beckman Coulter, Inc., Fullerton, Calif.

[21] Appl. No.: 08/978,731

[22] Filed: Nov. 26, 1997

[51] Int. Cl.[7] .................................................. G01N 21/80
[52] U.S. Cl. .............................. 436/74; 436/79; 436/164; 436/172; 422/57; 422/82.06; 422/82.07
[58] Field of Search .......................... 422/55, 57, 82.06, 422/82.07, 82.08, 82.09; 436/73, 74, 79, 164, 172, 163, 68

[56] References Cited

U.S. PATENT DOCUMENTS

| | | | |
|---|---|---|---|
| 3,862,302 | 1/1975 | Price et al. | 424/12 |
| 3,873,683 | 3/1975 | Fishbein | 424/12 |
| 3,955,928 | 5/1976 | Yee . | |
| 3,991,175 | 11/1976 | Grundman | 424/12 |
| 4,016,250 | 4/1977 | Saxena | 424/1 |
| 4,033,723 | 7/1977 | Givner et al. . | |
| 4,071,314 | 1/1978 | Prugnaud . | |
| 4,123,509 | 10/1978 | Banik et al. | 424/12 |
| 4,348,019 | 9/1982 | Cappel . | |
| 4,382,122 | 5/1983 | Mezel et al. . | |
| 4,433,057 | 2/1984 | de Gracia | 436/65 |
| 4,508,829 | 4/1985 | Sulitzeanu | 436/510 |
| 4,762,799 | 8/1988 | Seitz et al. | 436/79 |
| 4,943,522 | 7/1990 | Eisinger et al. . | |
| 4,985,204 | 1/1991 | Klose et al. | 422/56 |
| 5,128,019 | 7/1992 | Karpf et al. | 204/416 |

(List continued on next page.)

FOREIGN PATENT DOCUMENTS

| | | |
|---|---|---|
| 0319863 A2 | 6/1989 | European Pat. Off. . |
| 0767383 A1 | 4/1997 | European Pat. Off. . |
| WO 98/03497 A1 | 1/1998 | WIPO . |
| WO 99/02651 A1 | 1/1999 | WIPO . |

OTHER PUBLICATIONS

Seiler, K., et al: Characterization of Sodium–Selective Optode Membranes Based on Neutral Ionophores and Assay of Sodium in Plasma; Clinical Chemistry, vol. 37, No. 8; Aug. 1, 1991, pp. 1350–1355.

Dalgleish, Douglas G., et al; Ionic Strength Effects on the Electrophoretic Mobility of Casein–Coated Polystyrene Latex Particles; Journal of Colloid and Interface Science, vol. 108, No. 1, 1985, pp. 174–179.

Bakker E., et al; Ion–Selective Electrodes Based on Two Competitive Ionophores for Determining Effective Stability Constants of Ion–Carrier Complexes in Solvent Polymeric Membranes; Analytical Chemistry, vol. 70, No. 2, Jan. 15, 1998.

Nakamura, H., et al; Chromogenic Crown Ether Reagents for Spectrophotometric Determinations of Sodium and Potassium; Analytica Chimica Acta, 139 (1982), pp. 219–227.

Vaidya, Bikas, et al; Chromogenic and Fluorogenic Crown Ether Compounds for the Selective Extraction and Determination of Hg(II); Anal. Chem. 1995, 67, pp. 4101–4111.

Uniform Latex Particles; pp. 41–42; published by Bangs Laboratories, Inc. of Carmel, Indiana.

*Primary Examiner*—Jeffrey Snay
*Attorney, Agent, or Firm*—William H. May; Margaret A. Kivinski

[57] ABSTRACT

A pipettable detector comprises an aqueous suspension of particles which are essentially insoluble in a sample of a body fluid containing at least one target ion analyte of interest, the particles having uniformly distributed therein target and indicator ionophores which may be present in the same molecule or separate molecules. The indicator ionophore is capable of giving rise to a detectable signal following complexation of the target ionophore with the target ion from the sample. In a method of detecting an ionic analyte of interest in the sample of a bodily fluid, the sample is contacted with the detector. The indicator ionophore gives rise to a detectable signal following complexation of the target ionophore with the target ion from the sample, and the signal is then detected.

33 Claims, 1 Drawing Sheet

U.S. PATENT DOCUMENTS

| | | | |
|---|---|---|---|
| 5,133,934 | 7/1992 | Denton et al. | 422/56 |
| 5,145,789 | 9/1992 | Corti et al. | 436/530 |
| 5,185,270 | 2/1993 | Senyei et al. | 436/510 |
| 5,215,924 | 6/1993 | Rittersdorf et al. | 436/68 |
| 5,217,875 | 6/1993 | Karpf et al. | 435/34 |
| 5,266,486 | 11/1993 | Fraatz et al. | 435/287 |
| 5,372,936 | 12/1994 | Fraatz et al. | 435/34 |
| 5,405,975 | 4/1995 | Kuhn et al. | 422/82.06 X |
| 5,573,909 | 11/1996 | Singer et al. | 435/6 |
| 5,648,270 | 7/1997 | Kuhn et al. | 436/74 |

PIPETTABLE ION DETECTOR AND METHOD

BACKGROUND

The present invention is directed to systems for detecting target ions in body fluids.

There is a clinical need for detecting target ions in body fluids such as blood, plasma, urine, and spinal fluid. Among the ions that are commonly detected are $Ca^{++}$, $Na^+$, and $Cl^-$. One device used for detecting ions is an electrode, which produces a measurable electrical change upon contact with a fluid sample containing target ions.

Another device used for detecting ions is a thin film ion specific optode. These optodes contain a target ionophore which complexes with the target ion when present, and an indicator ionophore which provides an indication of such complexing, such as by a color change.

One problem associated with both of these devices is that they are incompatible with commonly used techniques for detecting organic compounds in body fluids. Organic components typically are detected using a photometric system where reagents are combined with a sample of the body fluid utilizing a pipette delivery system, and then the reagents are discarded after use. Contrarily, electrodes and thin film optodes are brought into contact with the sample, cleaned and then reused. Accordingly, clinical diagnostic equipment requires two different systems, one disposable, flowable reagent-based, and the other based on reused devices. This raises the cost of clinical diagnostic equipment because two independent measurement systems and the related hardware need to be combined in a single piece of equipment.

Another difficulty with conventional ion detection systems is the need to repeatedly clean the detection device after each use, which adds to the expense of the diagnostic process.

A third problem associated with conventional ion detector systems is that only low affinity ionophores can be used, because of the need to wash out the target ions from the electrode or optode after each use, so that the electrode or optode can be used for a new sample. If a high affinity ionophore is used, difficulty is experienced in washing out the target ion, with the result of lower throughput rates through an instrument.

Accordingly, there is a need for a method for detecting a target ion in a sample of a body fluid which can utilize equipment compatible with that used for analyzing organic compounds present in the body fluid, that does not require constant washing, and that can be used with high affinity ionophores.

SUMMARY

The present invention satisfies these needs, by providing an assay for detecting a target ion in a sample of a body fluid, utilizing a novel detector. The novel detector comprises a plurality of optodes suspended in an aqueous solution, i.e., a latex. Each optode comprises a particle having a diameter from about 10 nanometers to about 20 microns. The particles are insoluble in the body fluid and have distributed therein a target ionophore for the ion and an indicator ionophore. The target ionophore is capable of complexing with the target ion and the indicator ionophore is capable of giving rise to a detectable signal following complexation of the target ionophore with the target ion in the sample. The detector can be formed by application of standard ionophores to a conventional latex.

Each optode can comprise a plurality of target ionophores and indicator ionophores uniformly distributed in the particle. Moreover, each optode in a detector can comprise the same target ionophore or different target ionophores for detecting different ions. The detector can also comprise different optodes for detecting different target ions. The indicator ionophore can be a pH indicating chromoionophore or a pH indicating fluoroinophore.

The target ion can be selected from the group consisting of sodium, potassium, calcium, amonium and chloride. The detector can be used with a variety of body fluids, including urine and blood.

In the assay of the present invention, the sample is contacted with the novel detector in an analyzer. Typically the sample comprises a body fluid treated for analysis, such as being buffered with a pH buffer. The conditions, i.e., the pH and temperature, in the analyzer are maintained so that the target ionophore complexes with the target ion and the indicator ionophore gives rise to a detectable signal, such as a color change. Generally the temperature is maintained at room temperature. The detectable signal is then detected, typically using a spectrophotometer.

The present invention is directed not only to this detection method, but also the novel detector and the optodes that make up the detector. Due to the small size of the optodes, they are pipettable. Therefore, they are usable as any other flowable reagent used in commercial analyzers and thus are compatible with reagent based systems used for organic compounds. The optodes are inexpensive and disposable, so that they need not be cleaned and reused as is the case with electrodes and thin-film optodes. This greatly simplifies commercial clinical detection systems.

DRAWINGS

Figure 2:
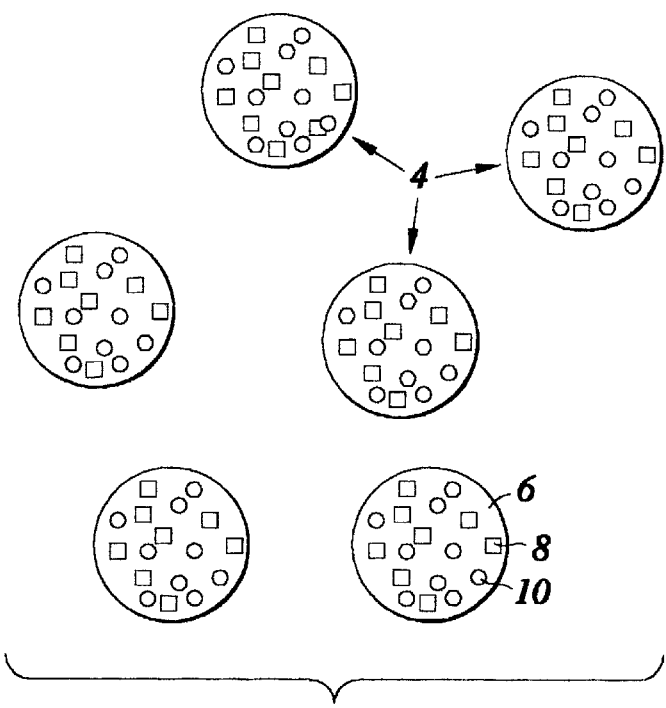

These and other features, aspects, and advantages of the present invention will become better understood from the following description, appended claims, and accompanying drawings where: FIG. 1 shows the absorbance spectra at two different pHs for a latex loaded with 126 nm oxazine 750 loaded latex. FIG. 2 depicts one embodiment of an ion detector device of the present invention.

DESCRIPTION

The present invention is directed to a method for detecting a target ion in a sample of a body fluid utilizing novel detectors that comprise a plurality of optodes suspended in an aqueous solution. FIG. 2 depicts one embodiment of novel detectors of the present invention. As shown in FIG. 2, each detector 2 may comprise a plurality of optode 4 suspended in an aqueous solution. Each optode 4 comprises a particle 6 that is sufficiently small that it is pipettable. Each particle 6 has distributed therein a target ionophore 8 for the ion 12 and an indicator ionophore 10 for indicating when the target ionophore 8 complexes with the target ion 12.

The invention is applicable to all types of body fluid samples including whole blood, spinal fluid, blood serum, urine, saliva, semen, tears, etc. The fluid sample can be assayed neat or after dilution or treatment with a buffer.

The optodes are formed by combining the indicators with latex particles. The latex particles are normally water-insoluble, hydrophobic organic polymeric particles such as polystyrene, polyparamethystyrene, polymethylmethacrylate, polyethylmethacrylate, polyethylene dimethacrylate, polyvinylidene chloride, polyvinyl chloride, polyvinyl acetate, polypropylene, methyl methacrylate-styrene copolymer, polyacrolein, polybutadiene and polydivinylbenzene.

The polymer latex commonly contains surfactants as stabilizers. However, the particles can have stabilizing charged groups on their surfaces, in which case surfactants are not required. Latex polymer particles can also benefit from incorporation of plasticizers.

In this invention other additives are sometimes used in the optode to enhance the extraction of target ion from the aqueous sample and migration of target ion into the organic particle phase. This can be effected by providing lipophilic anionic sites. Examples of such additives are:

NaTm($CF_3$)$_2$PB (sodium tetrakis[3,5-bis(trifluormethyl) phenyl]borate), ETH500 (tetradodecylammonium tetrakis (p-chloro-phenyl)borate), and KTpClPB (potassium tetrakis (4-chlorophenyl)borate).

The size of the latex particles is a function of competing criteria. One factor that affects the upper particle size is that the particles need to remain uniformly dispersed in an aqueous liquid suspension. This limits the particles to a maximum size of about 20 microns. The minimum particle size is established by the need to load the particles with the ionophores, and to avoid excessive light scattering during the detection process. The particles may be alternatively monitored one at a time (as, for instance in a flow cytometer). In this case the preferred size is in the range of 1–20 microns.

It has been determined that effective particles have a diameter of from about 10 nm to about 20 microns, preferably from about 50 nm to about 300 nm, and most preferably from about 100 nm to about 200 nm. The diameter of the particles is measured by a light scattering technique such as used by The Dawn Instrument manufactured by Wyatt Technology of Santa Barbara, Calif., U.S.A.

The present invention utilizes conventional ionophores. However, because the optodes need not be reused in the present invention, target ionophores with high affinity for the target ion can be used.

While the present discussion is directed primarily to chromionophores such as pH indicators as the indicator ionophore, the use of fluoroionophores is equally applicable. The signal is not restricted to color change; fluorescence or chemiluminescence modification is also useful. Many pH indicators (such as fluorescein and oxazine 750) show a change in fluorescence intensity or spectrum with different protonation states.

Table I provides examples of analytes and related target ionophores that are useful in the practice of the invention. Table II presents representative indicator ionophores, which typically are a chromionophore or a fluoroionophore, that can be used in the present invention.

TABLE I

| analyte | target ionophore |
|---|---|
| ammonia | monactin |
| ammonia | monactin |
| sodium | ETH2120 |
| sodium | ETH4120 |
| chloride | Chloro(octaethylporphyrinato)indium |
| potassium | valinomycin |
| calcium | ETH 1001 |

TABLE II

| indicator ionoiphores |
|---|
| ETH 5350 |
| ETH 2439 |
| ETH 5294 |
| ETH 2412 |

These are the common names for these materials. The chemical names are as follows:

| ETH# | CHEMICAL NAME |
|---|---|
| ETH2120 | [N,N,N',N'-Tetracyclohexyl-1,2-phenylenedioxydiacetamide] |
| ETH4120 | [4-Octadecanoyloxymethyl-N,N,N',N'-tetracyclohexyl-1,2-phenylenedioxydiacetamide] |
| ETH1001 | [(−)-R,R)-N,N'-Bis-[11-(ethoxycarbonyl) undecyl]-N,N'-4,5-tetramethyl-3,6-dioxaoctane-diamide; Diethyl N,N'-[(4R,5R)-4,5-dimethyl-1,8-dioxo-3,6-dioxaoctamethylene]bis(12-methylaminododecanoate)] |
| ETH5350 | [9-(Diethylamino)-5-](2-octyldecyl) imino]benzo[a]phenoxazine] |
| ETH2439 | [9-Dimethylamino-5-[4-16-butyl-2,14-dioxo-3,15-dioxaeicosyl)phenylimino]benzo[a]phenoxazine] |
| ETH5294 | [9-(Diethylamino)-5-octadecanoylimino-5H-benzo[a]phenoxazine] |
| ETH2412 | [5-Octadecanoyloxy-2-(4-nitrophenylazo)phenol] |

Generally, the two ionophores are different molecules. However, in the practice of this invention, it is possible to utilize a compound in which the indicator ionophore and the target ionophore are coupled into a single molecule. For example, Vaidya et al, Anal. Chem. 1995, 67, 4101–4111 disclose two useful novel crown ether compounds, N,N'-bis (2-hydroxy-5-nitrobenzyl)-4,13-diazadibenzo-18-crown-6 (CCE) and N,N'-bis(7-hydroxy-4-methylcoumarin-8-methylene)-4,13-diazadibenzo-18-crown-6(FCE), in which both functional molecular structure are present in the same compound. Likewise, Nakamura et al, Analytica Chimica Acta, 139 (1982) 219–227 which discloses the chromogenic crown ethers, (2-Hydroxy-3,5-dinitrophenyl)oxymethyl-18-crown-6 which detects potassium and (2-Hydroxy-3,5-dinitrophenyl)oxymethyl-15-crown-5 which detects sodium.

Each optode can contain different target ionophores and different indicator ionophores. Thus, a suspension of optodes can be used for detecting more than one target ion.

The solid latex particles of this invention preferably contain the indicator ionophore and the target ionophore in a molar ratio of from about 0.1 to 100, and more preferably a molar ratio of from about 0.5 to 25.

The solid latex particles typically contain the indicator ionophore and target ionophore in combined amounts equal to about 0.1 % to about 90% by weight based on the total weight of the loaded latex particles, and preferably from about 25% to about 50% by weight.

A satisfactory process for loading ionophores into latex particles is based upon processes used for coloring or dying latex particles. One typical process (attributed to John W. Vanderhoff of Lehigh University) is described on pages 41 and 42 of "Uniform Latex Particles" published by Bangs Laboratories, Inc. of Carmel, Ind.

The loading of the latex particles with the target ionophore and the signal ionophore can be accomplished in the following manner. The particles are temporarily swelled with the ionophores in a solvent solution to move the ionophores inside the particles; then the solvent is distilled off, leaving the ionophores stranded in the particles. The particles return close to their former size (no permanent swelling). The detailed steps are as follows:

a. The latex particles to be loaded are prepared at a solids content of <10% in water.

b. Oil-soluble target and indicator ionophores with some minimal water-solubility are selected. The ionophores preferably are predominantly oil-soluble, but must have a minimal solubility in water, as diffusion from the emulsion droplet through the aqueous phase to the latex particle is a requisite of this procedure.

c. The target and indicators are dissolved in xylene, methylene chloride, or other appropriate solvent such as benzene, toluene chloroform, dioxane dimethylformamide acetate, methyl ethyl ketone. The solvent selected should have the following properties: (1) low solubility in water; (2) a "good" solvent for the latex polymer; (3) a much lower vapor pressure than the ionophores.

d. The target and indicator ionophores concentration are used close to saturation to obtain maximum loading in the particles; however, if the solubility limit is exceeded some ionophore crystals may be formed in the aqueous phase. Therefore, the ionophore concentration should be at least slightly below saturation.

e. 1–3 parts of solvent solution per part of latex solids is used (for 0.1 micrometer particles use about 1 part solvent per part latex solids; for 1 micrometer particles use up to 3 parts solvent per part latex solids). The proportion of ionophore solution that is mixed with the latex must be such that all of it can be absorbed by the latex particles. Otherwise, some ionophore emulsion droplets are left unabsorbed and can form dye precipitate in the water when the solvent is removed. The proportion of solvent that can be absorbed by the particles increases with increasing particle size and decreasing polymer/water interfacial tension.

f. The aqueous latex suspension (<10% solids) is gently stirred, adding ionophore solvent solution drop wise and very slowly. Periodically stop stirring to see if solvent droplets float to the surface (xylene) or settle out ($CH_2Cl_2$) to form a separate phase. If phase separation occurs, continue stirring, but slow down the rate of addition of ionophore solution so that solvent is taken up by the particles as fast as it is added. The proper addition rate can be only one drop every few seconds. This addition step can take from a few hours to several days. If ionophore solution is added too rapidly, it can form too much of the solvent-in-water emulsion. Then the latex particles can dissolve in the emulsified solvent phase (instead of solvent and ionophores dissolving in the polymer particles), creating large, "sticky" globules of ionophore/solvent/polymer. Swelling is complete when particles have taken up all solvent and ionophores when stirring is stopped, and solvent no longer forms a separate phase.

g. Solvent is distilled out using a rotary evaporator (such as made by Rinco or Buchi/Brinkmann) under reduced pressure. The suspension can be warmed to about 40–50° C. to increase vapor pressure. The solvent distills out with water to form an azeotrope, leaving the ionophores behind in the particles. Distillation is continued until no further solvent comes over with the water. It can be necessary to add water periodically to prevent the latex from drying out. Surfactant can be added in this step to promote particle stability, if necessary.

An aqueous suspension of the detector, the sample, and any buffer present are usually added to a reaction cell or cuvette in an analyzer. This provides an essentially uniform dispersion of the latex particles in the buffered sample.

The optodes are used in a analyzer by contacting a sample with a plurality of the optodes suspended in an aqueous solution. When a target ion is present, the target ionophore, which preferably is specific for the target ion, complexes with the target ion and the indicator ionophore provides a detectable signal as a result of complexation of the target ionophore with the target ion. The pH and temperature in the analyzer are maintained so this complexing can occur and the indicator ionophore can produce the detectable signal.

The aqueous suspension of loaded latex and the sample are usually added to a reaction vessel by pipette. The resultant mixture is an essentially uniform dispersion of the latex particles in the pH buffered reaction mixture.

A light beam is then passed through the cuvette or reaction cell and the light not absorbed by the contents of the cuvette is sampled and analyzed by a photodetector. The incident light can be so-called "white" light and the light not absorbed is separated into its colored components for analysis.

Alternatively, if the indicator ionophore develops a fluorescence signal, exciting light passes into the cuvette, and a photodetector measures emitted fluorescent light.

Conventional light sources and detection systems can be used. Each ion of interest when contacted with the target ionophore causes a change in the signal produced by the signal ionophore. Thus, the concentration in the cuvette of a target ion of interest can be determined by analyzing the light which reaches the photodetector.

Frequently, to determine the concentration of the target ions, it is necessary to control the concentration of hydrogen ions. This is most readily accomplished by keeping the hydrogen ion concentration relatively constant with pH buffered reaction mixtures. Some samples are inherently buffered. Blood, serum, and plasma are examples of such buffered samples. Different specimens have different pH's, so if inherent buffering of the sample is used, the pH must be independently measured to determine the target ion concentration.

However, it is preferred to control the pH of the reaction mixture with a buffer. This reduces effects due to variations in sample pH, and allows selection of an optimal pH for the optode. The proportion of sample in a reaction mixture is in part determined by the buffering capacity of the sample. A small enough proportion of sample must be selected to allow the buffer to dominate the pH of the mixture.

pH indicating ionophores of choice have high pK and the latex suspensions containing these pH indicators preferably are buffered near this pK. Thus, the aqueous suspension is normally buffered to maintain the pH at or around the pKa at which the pH indicator ionophore changes color. Appropriate buffer systems for the pH indicators systems discussed above are already known. Typical buffers are sodium phosphate and tris (hydroxymethyl) aminomethane. Thus, in the assay, it is preferred that the pH of the reaction mixture is maintained at about the pH at which the indicator ionophore changes color.

It is possible to perform multiple ion analyses simultaneously on a single sample by using a latex cocktail with different color indicator ionophores associated with different target ionophores. Alternatively similar colors may be used if the optodes are read one at a time as in a flow cytometer.

FIG. 1 is a spectrophotometer tracing of the optical density of suspensions of oxazine 750 loaded latex at different pH's. Trace 2 shows loss of the peak absorbance in the 620 nm region after the pH of the medium was raised above 10 with sodium hydroxide. This was accompanied by a vivid color change from blue to pink. This demonstrates the retention of pH responsivity when the indicator is loaded into polystyrene latex which is a necessary condition to a satisfactory optode.

The following examples are illustrative of the invention.

EXAMPLE I

Calcium Assay

Latex Formulation (latex 1)

120 nm polystyrene latex loaded using xylene as the solvent with

8% by weight ETH 1001 calcium ionophore

2% by weight ETH 5294 pH indicator

4% by weight NaTm $(CF_3)_2$PB lipophilic anionic site additive diluted to 1% solids in Assay Buffer 1, following the "loading of particles" method described above.

Assay Buffer 1

$10^{-3}$M citric acid, adjusted to pH 6.5 with 0.1 N NaOH

Reaction Mixture latex suspended to 0.1% solids (30 microliters latex 1) 5% serum by volume (sample) (15 microliters)

balance buffer to a total volume of 300 microliters (255 microliters)

Measurement measure absorbance at 660 nm in 5 mm cuvette

EXAMPLE II

Potassium Assay (Prospective Example)

Latex Formulation (latex 11)

120 nm polystyrene latex loaded using xylene as the solvent with

1% by weight Valinomycin potassium ionophore 0.5% by weight ETH5294 pH indicator 0.5% by weight KTpClPB lipophilic anionic site additive diluted to 1% solids in Assay Buffer II, following the "loading of particles" method described above.

Assay Buffer II 0.02 M sodium acetate acid, adjusted to pH 5.1 with 1 M acetic acid Reaction Mixture latex suspended to 0.1% solids (30 microliters latex 11) 5% plasma by volume (sample) (15 microliters)

balance buffer to a total volume of 300 microliters (255 microliters)

Measurement measure absorbance at 660 nm in 5 mm cuvette

Although the present invention has described in considerable detail with reference to certain preferred versions thereof, other versions are possible. For example, the present invention has been described where the detector comprises a plurality of optodes, each optode being capable of detecting a single target ion, and all of the optodes being for that particular target ion. Alternatively, the optodes can each detect multiple target ions, or a detector can comprise a plurality of different optodes, for detecting a plurality of different target ions. Alternatively, the detector can contain a single large optode, in which case the upper limit on the particle size is not about 20 microns, but rather is about 200 microns. The maximum size in this case is determined by the size of the flow conduits or the probes or pipettes used for transporting the optode.

Thus, the scope of the appended claims is not limited to the description of the preferred versions contained herein.

The reader's attention is directed to all papers and documents which may be filed concurrently with this specification and which are open to public inspection with this specification, and the contents of all such papers and documents are incorporated herein by reference.

All the features disclosed in this specification (including any accompanying claims, abstract, and drawings), and/or all of the steps or any method or process so disclosed, may be combined in any combination, except combinations where at least some of such features and/or steps are mutually exclusive.

Each feature disclosed in this specification (including any accompanying claims, abstract, and drawings), may be replaced by alternative features serving the same, equivalent or similar purpose, unless expressly stated otherwise. Thus, unless expressly stated otherwise, each feature disclosed is one example only of a generic series of equivalent or similar features.

What is claimed is:

1. An ion detector for detecting a target ion present in a sample of a body fluid, the detector comprising:
   a plurality of optodes suspended in an aqueous solution, each optode comprising
   a particle having a diameter of from about 10 nm to about 20 microns, the particles being insoluble in the body fluid and having distributed therein a target ionophore for the target ion and an indicator ionophore, the target ionophore being capable of complexing with the target ion and the indicator ionophore being capable of giving rise to a detectable signal following complexation of the target ionophore with the target ion in the sample.

2. The detector of claim 1 wherein the optodes are pipettable.

3. The detector of claim 1 wherein each optode comprises a plurality of target ionophores and indicator ionophores uniformly distributed in the particle.

4. The detector of claim 1 wherein the target ionophore and the indicator ionophore are present in the same molecule.

5. The detector of claim 1 wherein the diameter of each particle is from about 50 nm to about 300 nm.

6. The detector of claim 1 wherein the diameter of the particle is from about 100 nm to about 200 nm.

7. The detector of claim 1 wherein each optode comprises the same target ionophore.

8. The detector of claim 1 wherein at least some of the optodes comprise different target ionophores for different target ions.

9. The detector in claim 1 wherein the detector comprises different optodes for detecting different target ions.

10. The detector of claim 1 wherein the particles are water-insoluble, hydrophobic organic polymeric particles.

11. The detector of claim 1 wherein the indicator ionophore is a pH indicating chromionophore.

12. The detector of claim 1 wherein one of the ionophores is a chromionophore.

13. The detector of claim 1 wherein one of the ionophores is a fluorionophore.

14. The detector of claim 1 wherein one of the ionophores is a pH indicator.

15. The detector of claim 1 wherein the indicator ionophore is a pH indicating fluoroinophore.

16. A method for detecting a target ion in a sample of a body fluid comprising the steps of:

a) contacting the sample with a detector in an analyzer, the detector comprising a plurality of optodes suspended in an aqueous suspension, each optode comprising a particle having a diameter of from about 10 nm to about 20 microns, the particles being insoluble in the body fluid and having distributed therein a target ionophore for the target ion and an indicator ionophore, the target ionophore being capable of complexing with the target ion and the indicator ionophore being capable of giving rise to a detectable signal following complexation of the target ionophore with the target ion in the sample;

b) maintaining the conditions in the analyzer so that the target ionophore complexes with the target ion and the indicator ionophore gives rise to a detectable signal; and b) detecting the detectable signal.

17. The method of claim 16 wherein the body fluid is urine or blood.

18. The method of claim 16 wherein the step of detecting of the signal comprises passing light through the aqueous suspension.

19. The method of claim 16 wherein the target ion is selected from the group consisting of sodium, potassium, calcium, ammonium, and chloride.

20. The method of claim 16 wherein the body fluid contains multiple ions of interest and multiple ions are detected.

21. The method of claim 16 wherein the step of detecting is carried out using a spectrophotometer.

22. The method of claim 16 wherein the step of contacting comprises adding the detector to the sample by pipetting.

23. The method of claim 16 wherein each optode comprises a plurality of target ionophores and indicator ionophores uniformly distributed in the particle.

24. The method of claim 16 wherein the target ionophore and the indicator ionophore are present in the same molecule.

25. The method of claim 16 wherein the diameter of each particle is from about 50 nm to about 300 nm.

26. The method of claim 16 wherein the diameter of the particle is from about 100 nm to about 200 nm.

27. The method of claim 16 wherein each optode comprises the same target ionophore.

28. The method of claim 16 wherein at least some of the optodes comprise different target ionophores for different target ions.

29. The method of claim 16 wherein the detector comprises different optodes for detecting different target ions.

30. The method of claim 16 wherein the sample comprises body fluid buffered with a buffer.

31. An optode for detecting a target ion in a body fluid, the optode comprising a water insoluble particle having a diameter of from about 10 nm to about 200 microns, the particle being insoluble in the body fluid and having distributed therein a target ionophore for the ion and an indicator ionophore, the target ionophore being capable of complexing with the target ion and the indicator ionophore being capable of giving rise to a detectable signal following complexation of the target ionophore with the target ion in the sample.

32. The detector of claim 31 wherein the diameter of the particle is from about 10 nm to about 20 microns.

33. The detector of claim 31 wherein comprising a plurality of target ionophores and indicator ionophores uniformly distributed in the particle.

* * * * *